United States Patent [19]

Janulis

[11] Patent Number: 5,110,984
[45] Date of Patent: May 5, 1992

[54] PROCESS FOR INCREASING THE YIELD OF PURIFIED ISOPHTHALIC ACID AND REDUCING WASTE-WATER TREATMENT A

[75] Inventor: Rose M. Janulis, Downers Grove, Ill.

[73] Assignee: Amoco Corporation, Chicago, Ill.

[21] Appl. No.: 610,147

[22] Filed: Nov. 6, 1990

[51] Int. Cl.$^5$ .................... C07C 51/487; C07C 51/43
[52] U.S. Cl. .................... 562/487; 562/486; 502/185
[58] Field of Search ................ 562/486, 487; 502/185

[56] References Cited

U.S. PATENT DOCUMENTS

| | | | |
|---|---|---|---|
| 4,391,985 | 7/1983 | Hook et al. | 562/414 |
| 4,405,809 | 9/1983 | Stech et al. | 562/487 |
| 4,933,492 | 6/1990 | Schroeder et al. | 562/487 |

*Primary Examiner*—Jose G. Dees
*Assistant Examiner*—Vera C. Clarke

*Attorney, Agent, or Firm*—Margaret M. Duncan; William H. Magidson; Frank J. Sroka

[57] ABSTRACT

The invention is an improved method of purification of isophthalic acid comprising recycling a portion of the mother liquor solution into the feed solution of an isophthalic acid purification process. The improved method comprises the following steps:

(a) dissolving crude isophthalic acid in a feed solution comprising a polar solvent at a temperature of from about 100° C. to about 300° C.;

(b) crystallizing the isophthalic acid by cooling the solution of step (a) to a temperature of from about 35° C. to about 120° C.;

(c) separating the isophthalic acid crystals from the solution and drying the crystals; and (d) recycling a portion of the solution remaining after the separation of isophthalic acid crystals back to the feed solution.

9 Claims, 1 Drawing Sheet

PROCESS FOR INCREASING THE YIELD OF PURIFIED ISOPHTHALIC ACID AND REDUCING WASTE-WATER TREATMENT A

This invention relates generally to a process for making purified isophthalic acid. More particularly, the invention relates to a process for increasing the yield of purified isophthalic acid and reducing water consumption and waste-water treatment by recycling a portion of the purified isophthalic acid mother liquor stream.

BACKGROUND OF THE INVENTION

Purified isophthalic acid is a precursor material for the manufacture of various polymeric materials including unsaturated polyesters. It is derived from less pure "crude" isophthalic acid by purification which can be accomplished by dissolving the crude isophthalic acid in a feed solution comprising a polar solvent at a high temperature, reducing the temperature to effect crystallization of the isophthalic acid, and separating the purified isophthalic acid crystals from the aqueous solution.

Another method of purification of crude isophthalic acid utilizes hydrogen and a noble metal catalyst such as described in Meyer, U.S. Pat. No. 3,584,039 and Stech et al., U.S. Pat. No. 4,405,809 for purification of crude terephthalic acid. The purification process involves dissolving crude isophthalic acid in hot deionized water, contacting the solution with hydrogen as a reducing agent and passing the solution over a fixed bed catalyst containing a noble metal such as palladium on a carbon support, as described in Pohlmann, U.S. Pat. No. 3,726,915 for the purification of crude terephthalic acid, incorporated by reference herein. The isophthalic acid solution is then cooled to a temperature which effects crystallization of the isophthalic acid, which is separated from the solution. More recently, in Schroeder et al., U.S. Pat. No. 4,933,492, which is incorporated by reference herein, an improved isophthalic acid purification process has been described which utilizes a catalyst system comprising at least two of palladium, platinum, rhodium, ruthenium, osmium, and iridium-containing components supported on active carbon carrier particles.

Optimally, the isophthalic acid purification process lowers the levels of organic intermediates, primarily 3-carboxybenzaldehyde (3-CBA), and inorganic contaminants and colored compounds. The color level of purified isophthalic acid is generally measured directly either by measuring the optical density (O.D.) of solutions of purified isophthalic acid or the b*-valve of the solid purified isophthalic acid. The optical density of purified isophthalic acid is measured as the absorbance of light at 340 and 400 nm in a solvent such as sodium hydroxide or ammonium hydroxide.

The measurement of the b*-value of a solid on the Hunter Color Scale is described in Hunter, *The Measurement of Appearance*, Chapter 8, pp. 102-132, John Wiley & Sons, N.Y., N.Y. (1975), and in Wyszecki et al., *Color Science, Concepts and Methods, Quantitative Data and Formulae*, 2d Ed., pp. 166-168, John Wiley & Sons, N.Y., N.Y. (1982). A specific description of measuring the b*-value of isophthalic acid is described in the above-mentioned U.S. Pat. No. 4,933,492.

The overall effect of the purification process for isophthalic acid is to convert impurities which normally crystallize with isophthalic acid into compounds which can be separated from the isophthalic acid by pratical techniques. After separation of the purified isophthalic acid crystals, all of the remaining mother liquor stream, which comprises isophthalic acid and impurities dissolved in water, is typically directed to a waste treatment unit for disposal. However, it is advantageous to minimize waste streams due to environmental and economic concerns.

Before this invention, it was believed that in order to maintain purity requirements, mother liquor from an isophthalic acid purification process must be discarded to the waste stream. For example, in the purification by hydrogenation over noble metal catalysts of other aromatic polycarboxylic acids such as terephthalic acid, the practice of recycle has been prohibited due to limitations in the level of the impurity, p-toluic acid in the purified terephthalic acid. Surprisingly, it has been found that up to about 60 percent of mother liquor in an isophthalic acid purification process can be recylcled to the feed stream without significant reduction in quality of the isophthalic acid product as measured by optical densities and b*-valve. This discovery permits a significant reduction in the waste stream. In a preferable process according to this invention, about 20 percent to about 60 percent of the mother liquor can be recycled without significantly affecting product quality. A typical recycle amount would be about 25 percent. This recycle offers environmental advantages including reducing water consumption in the feed stream and reducing the generation of waste-water and the total organic carbon sent to the waste-water treatment unit.

SUMMARY OF THE INVENTION

The invention is an improved method of purification of isophthalic acid comprising recycling a portion of the mother liquor solution into the feed solution of an isophthalic acid purification process. The improved method comprises the following steps:

(a) dissolving crude isophthalic acid in a feed solution comprising a polar solvent at a temperature of from about 100° C. to about 300° C.;

(b) crystallizing the isophthalic acid by cooling the solution of step (a) to a temperature of from about 35° C. to about 120° C.;

(c) separating the isophthalic acid crystals from the solution and drying the crystals; and (d) recycling a portion of the solution remaining after the separation of isophthalic acid crystals back to the feed solution.

In a preferred embodiment, the invention comprises the following steps:

(a) dissolving crude isophthalic acid in a feed solution comprising a polar solvent at a temperature of from about 100° C. to about 300° C.;

(b) passing the hot feed solution containing isophthalic acid at a pressure sufficient to maintain the solution substantially in the liquid phase, through a particulate catalyst bed in the presence of hydrogen, the catalyst bed comprising at least one Group VII noble metal-containing component selected from the group consisting of palladium-, platinum-, rhodium-, ruthenium-, osmium-, iridium-containing components and mixtures thereof supported on active carbon carrier particles;

(c) cooling the solution to a temperature of from about 35° C. to about 120° C. to effect separation of the resulting purified isophthalic acid from the solution by crystallization;

(d) recovering and drying the crystallized, purified isophthalic acid; and (e) recycling a portion of the solution remaining after the recovery of the isophthalic acid crystals back to the feed solution.

Surpisingly, it has been found that the recycle of the mother liquor solution back into the feed stream of an isophthalic acid purification process does not affect the quality of the final purified isophthalic acid product. The advantages of recycle include improving isophthalic acid yields, while reducing water consumption, generation of waste-water and the total organic carbon sent to the waste-water treatment unit.

DETAILED DESCRIPTION OF THE INVENTION

Figure 1:
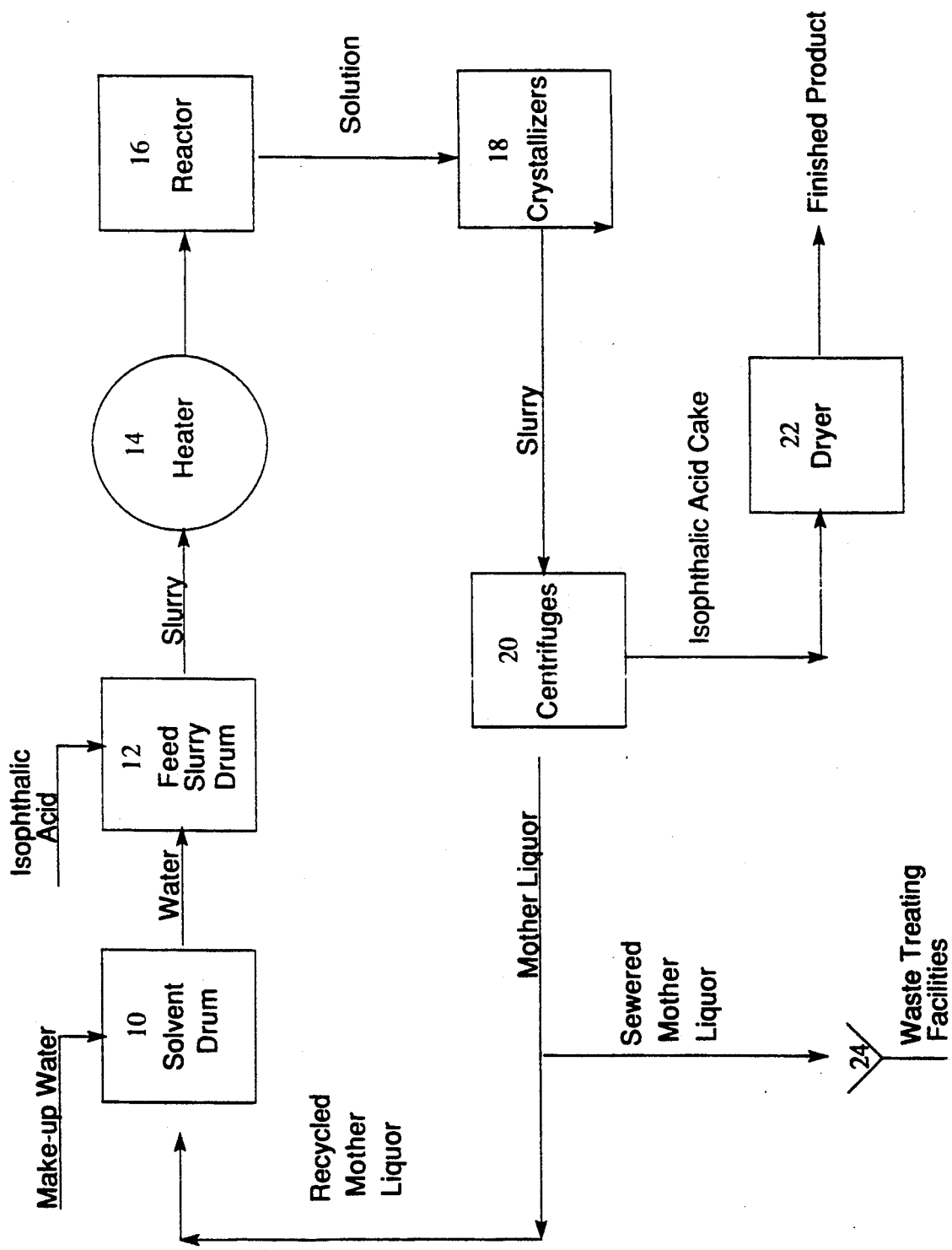
FIG. 1 is a simplified block flow diagram of a preferred embodiment of the purification process of the invention.

The method of this invention is particularly suitable for use in the purification of crude isophthalic acid prepared by the continuous catalytic, liquid-phase oxidation of m-xylene in a solvent. Suitable solvents for use in the catalytic, liquid-phase oxidation of m-xylene include any apliphatic $C_2$–$C_6$ monocarboxylic acid such as acetic acid, propionic acid, n-butyric acid, isobutyric acid, n-valeric acid, trimethylacetic acid, and caproic acid, and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation of the crude isophthalic acid is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude isophthalic acid product from the product stream, at least a portion of the mother liquor (solvent) in the resulting product stream is generally recycled to the reactor.

The source of molecular oxygen employed in the oxidation step of the method for producing crude isophthalic acid can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method for producing crude isophthalic acid comprises cobalt, manganese, and bromine components, and can additionally comprise accelerators known in the art. The weight ratio of cobalt (calculated as elemental cobalt) in the cobalt component of the catalyst-to-m-xylene in the liquid-phase oxidation is in the range of from about 0.2 to about 10 milligram atoms (mga) per gram mole of m-xylene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid phase oxidation is in the range of from about 0.2 to about 1.5 mga per mga of total cobalt and manganese.

Each of the cobalt and manganese and bromine components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion releases from the organic bromides at the oxidation operating conditions can be readily determined by known analytical means.

In operation, the minimum pressure at which the oxidation reactor is maintained is that pressure which will maintain a substantial liquid phase of solvent within the reactor. The solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm² to about 35 kg/cm², and typically are in the range from about 10 kg/cm² to about 30 kg/cm². The temperature range within the oxidation reactor is generally from about 120° C., preferably from about 150° C. to about 240° C. The solvent residence time in the oxidation reactor is generally from about 20 to about 150 minutes and preferably from about 30 to about 120 minutes.

The resulting oxidation reactor product contains relatively impure or crude isophthalic acid that includes relatively large amounts of impurities such as 3-carboxybenzaldehyde, which impurities can be present in amounts up to about 10,000 parts per million parts of isophthalic acid, by weight. These impurities adversely affect the isophthalic acid polymerization reactions which produce unsaturated polyesters as well as may cause undesirable coloring of the resulting unsaturated polyester polymers and other polymers using isophthalic acid. The purification of crude isophthalic acid can be accomplished by dissolving the crude isophthalic acid in an aqueous solution at an elevated temperature of about 100° C. to about 300° C., reducing the temperature to about 35° C. to about 120° C., in order to crystallize the isophthalic acid and separating the purified isophthalic acid crystals from the aqueous solution.

In a preferred embodiment, the purification process of the invention is conducted at an elevated temperature and pressure in a fixed catalyst bed. Both down-flow and up-flow reactors can be used. The crude isophthalic acid to be purified is dissolved in a polar solvent such as water. Water is the preferred solvent; however, other suitable polar solvents are the relatively lower molecule weight alkyl carboxylic acids, alone or admixed with water. Hydrogenation of 3-carboxbenzaldehyde to m-toluic acid is one of the principal reactions that occurs in the catalyst bed.

Reactor, and thus isophthalic acid solution, temperatures during purification can be in the range of about 100° C. (about 212° F.) to about 300° C. (about 572° F.). Preferably the temperatures are in the range of about 200° C. (about 392° F.) to about 250° C. (about 482° F.). Reactor pressure conditions primarily depend upon the temperature at which the purification process is carried out. Inasmuch as the temperatures at which practical amounts of the impure isophthalic acid may be dissolved are substantially above the normal boiling point of the polar solvent, the process pressures are necessarily considerably above atmospheric pressure to maintain the isophthalic acid solution in liquid phase. If the reactor has a head space, the reactor pressure can be maintained by gaseous hydrogen alone in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 100 to about 1000 pounds per square inch gauge (psig), and usually is in the range of about 350 psig to about 450 psig.

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the isophthalic acid solution present is the hydrogen partial pressure in the reactor vapor space. Alternatively, if hydrogen is fed in admixture with an inert gas such as nitrogen, the difference between the actual reactor pressure and the vapor pressure of the isophthalic acid solution present is the combined partial pressure of hydrogen and the inert gas admixed therewith. In this case, the hydrogen partial pressure can be calculated from the known relative amounts of hydrogen and inert gas present in the admixture.

In the operating mode where process control is effected by adjusting the hydrogen partial pressure, the hydrogen partial presure in the reactor preferably is in the range of about 10 psi to about 200 psi, or higher, depending upon the service pressure rating of the reactor, the degree of contamination of the impure isophthalic acid, the activity and age of the particular catalyst employed, and like processing considerations.

A suitable catalyst for the purification process of the preferred embodiment of the invention is a palladium-on-carbon catalyst which can be obtained, for example, from Engelhard Corporation, Newark, N. J., under the designation "Palladium on Activated Carbon Granules (Carbon Code CG-5)." Similarly, other suitable Group VII noble metal-containing catalysts such as rhodium-on-carbon catalysts can be obtained from Englehard Corporation, under the designations "Rhodium on Activated Carbon Granules (Carbon Code CG-5)" and "Rhodium on Activated Carbon Granules (Carbon Code CG-21)." Both of these rhodium-on-carbon catalysts have a $N_2$ BET surface area of about 1,000 $m^2$/gram and have a particle size of $4 \times 8$ mesh, U.S. Sieve Series. Other suitable rhodium-on-carbon and palladium-on-carbon catalysts of similar size and surface area are available from Johnson Matthey Inc., Seabrook, N. H. under the designation "11766 Rhodium, 1% on Steam Activated Carbon Granules, Anhydrous." Similarly, suitable ruthenium-on-carbon, platinum-on-carbon and iridium-on-carbon catalysts are commercially available.

The preferred catalyst carrier is active carbon, usually that derived from coconut charcoal in the form of granules having a surface area of at least about 600 $m^2$/g ($N_2$; BET Method), preferably about 800 $m^2$/g to about 1,500 $m^2$/g. However, other porous carbonaceous supports or substrates can be used as long as the surface area requirements can be met. In addition to coconut charcoal, activated carbon derived from other plant or animal sources can be utilized.

The loading of each of the palladium, ruthenium, rhodium, platinum, osmium or iridium employed on the carrier is in the range of about 0.01 weight percent to about 2 weight percent, based on the total weight of the catalyst, i.e., metal plus active carbon carrier, and calculated as elemental metal. Preferably, the loading of each catalyst metal employed is about 0.5 weight percent.

In one embodiment of the purification process of the present invention, one or more of the Group VIII noble metal-containing components is supported on the same active carbon carrier particles, and thus there is a substantially uniform distribution of one or more of the Group VIII noble metal-containing components throughout the catalyst bed. In this embodiment, a particular active carbon carrier particle contains one or more of the Group VIII noble metal-containing components, and the relative amounts of the Group VIII noble metals in the catalyst bed are controlled by the relative amounts of the Group VIII noble metals on each catalyst particle.

In the alternative, and preferably, one Group VIII noble metal-containing component is supported on a first group of active carbon carrier particles, and a second Group VIII noble metal-containing component is supported on a second group of the active carbon carrier particles. The aforesaid first group of particles is separate and distinct from the aforesaid second group of particles. In this embodiment, a particular active carbon carrier particle contains only one Group VIII noble metal-containing component; and the relative amounts of the Group VIII noble metals in the catalyst bed are controlled either by the relative amounts of the Group VIII noble metal-containing components employed in their respective groups of active carbon carrier particles or by the relative amounts of active carbon carrier particles employed in their respective groups of active carbon carrier particles. In this embodiment, when each of the first and second groups of active carbon carrier particles are uniformly distributed throughout the catalyst bed, the Group VIII noble metal-containing components are also uniformly distributed throughout the catalyst bed. Alternatively in this embodiment, the catalyst bed is layered and has (1) at least one layer comprising substantially only the aforesaid first group of particles and (2) at least one layer comprising substantially only the aforesaid second group of particles, and thus the Group VIII noble metal-containing components are not uniformly distributed throughout the catalyst bed.

In this later case of a layered bed, the aqueous isophthalic acid solution is passed first through a first layer comprising substantially only the aforesaid first group of particles containing only a first Group VIII noble metal-containing component and then through a second layer comprising substantially only the aforesaid second group of particles containing only the second Group VIII noble metal-containing component. Typically the weight ratio of the first layer to the second layer is in the range of from about 1:100, preferably from about 1:20 to about 1:2, and most preferably about 1:4. Similarly, the residence time of the aqueous isophthalic acid solution in the first layer is from about 1:2 to about 1:100 of the total residence time of the solution in the catalyst bed. Thereafter, the aqueous solution is withdrawn from the catalyst bed directly or after passing the aqueous solution through a third layer comprising, for example, substantially only either the aforesaid first group of particles containing only the first Group VIII noble metal-containing component or a third group of particles comprising a third Group VIII noble metal-containing component.

The aqueous solution of isophthalic acid is cooled to crystallize the isophthalic acid in one or more crystallizers. During the crystallization, a portion of the aqueous solvent may be removed as a vapor from the slurry of isophthalic acid crystals. After cooling to a final crystallization temperature of from about 35° C. to about 120° C., the isophthalic acid crystals are recovered from the mother liquor. A solid-liquid separation device such as a centrifuge or filter may be employed for separating mother liquor from the crystals. The crystals may be washed with additional solvent within the solid-liquid separation device, or the crystals may be combined with additional solvent and sent to a second solid-liquid separation step. The washed isophthalic acid crystals are then passed to a dryer and heated to a temperature of about 100° C. to about 180° C. to remove liquor remaining on the crystals in order to allow the crystals to be packaged.

Prior to the invention disclosed herein, the isophthalic acid purification process described above operated as a "once through" system. The solvent for the process, typically water, is mixed with the crude isophthalic acid in the feed preparation section of the unit. This slurry is heated to dissolve the crude isophthalic acid in the solvent and preferably passed through a reactor containing a fixed catalyst bed. The reactor effluent is crystallized and the isophthalic acid crystals recovered and separated from the solvent through the use of a centrifuge. The isophthalic acid cake from the centrifuge is dried, resulting in the final purified isophthalic acid product. The mother liquor from the centrifuges, which is saturated with isophthalic acid is then sent to a waste treatment unit.

As shown in FIG. 1, in the preferred purification process of this invention, a portion of the mother liquor is recycled back into the feed stream via solvent drum 10, where it is mixed with the solvent and fed into the crude isophthalic acid feed slurry drum 12. This mixture is then passed through heater 14 and into reactor 16. In the reactor, the mixture is passed over a catalyst bed as described above. Next, the temperature of the mixture is lowered to effect crystallization in crystallizers 18 and passed into centrifuges 20, where the purified isophthalic acid crystals are separated and sent to dryer 22.

Previously, it had been thought that the mother liquor which contains impurities must be entirely discarded, that is, sent to a waste-water treatment unit, in order to produce the desired quality of purified isophthalic acid. For example, in the purification by hydrogenation over noble metal catalysts of other aromatic polycarboxylic acids such as terephthalic acid, the practice of recycle has been prohibited due to limitations in the level of the impurity, p-toluic acid in the purified terephthalic acid. In the purification of isophthalic acid, it has been unexpectedly found that from about 20 percent to about 60 percent of the mother liquor from the centrifuges 20 can be recycled with no adverse effects on the quality of the purified isophthalic acid or on the purification process.

The percentage of mother liquor which is recycled is critical to the present invention in that the quality of the isophthalic acid may be adversely affected if the level of recycle is too high. The percentage of mother liquor recycle depends on the quality of crude isophthalic acid being purified. For a crude isophthalic acid which is manufactured as described above, the range of recycle which will result in an acceptable purified isophthalic acid product is from about 20 percent to about 60 percent of the mother liquor stream. Of course, those skilled in the art will recognize that this range may be broadened as the oxidation and purification unit operations are optimized with the use of the invention disclosed herein. There are several advantages to the recycling process of the invention including reducing water usage in the initial slurry preparation, lowering wastewater treatment costs and increasing product yield.

The present invention will be more clearly understood from the following specific examples.

EXAMPLES 1 AND 2

In Examples 1 and 2, an isophthalic acid purification unit was operated with a reactor feed slurry concentration of about 29.1 wt. % to about 38.5 wt. %, at reaction conditions of a temperature of between about 220.5° C. and about 222.2° C. (about 429° F. to about 432° F.) and at a pressure of about 440 psig. The reactor was of the down-flow type and contained a catalyst bed comprised of particulate palladium-on-carbon and rhodium-on-carbon catalysts (Engelhard Corporation) in a layered bed configuration as described above. In Example 1, the entire mother liquor stream was sent to waste treatment. In Example 2, 25 percent of the mother liquor stream was recycled to the solvent drum and, in turn, was used in preparation of the reactor feed slurry. The purified isophthalic acid produced in Examples 1 and 2 was tested for b*-value and optical densities at 340 and 400 nm. The results are reported in Table 1 below.

TABLE 1

|  | Crude | Purified |
|---|---|---|
| Example 1 | | |
| b* - value | 4.44–5.22 | 1.45–1.78 |
| Optical density at 340 nm | 2.01–2.02 | 1.04–1.28 |
| Optical density at 400 nm | .225–.250 | .065–.080 |
| 3-carboxybenzaldehyde ppm | 243–433 | 5–22 |
| Example 2 | | |
| b* - value | 5.02–5.41 | 1.69–1.90 |
| Optical density at 340 nm | 1.90–2.00 | 1.14–1.21 |
| Optical density at 400 nm | .280–.325 | .070–.085 |
| 3-carboxybenzaldehyde ppm | 455–637 | 21–24 |

Table 1 demonstrates that the relative improvement from the crude to the purified isophthalic acid in the optical quality measurements of b*-value and optical density was not adversely affected when a portion of the mother liquor stream was recycled. The optical quality of purified isophthalic acid in Example 2 is within the same range of values as Example 1, which represents acceptable final product quality. Furthermore, the use of mother liquor recycle did not affect the impurity level of purified isophthalic acid as measured by the concentration of 3-carboxybenzaldehyde. The measurement of optical quality and 3-carboxybenzaldehyde concentration are considered to be indicators of the processability of isophthalic acid in an unsaturated polyester process and the ultimate quality of unsaturated polyester or other polymeric material made from the purified isophthalic acid.

In another test run, about 40 percent of the mother liquor stream was recycled, again with no detrimental effect to the final purified isophthalic acid product. From the above description, it is apparent that, while only certain embodiments have been set forth, alternative embodiments and various modifications will be apparent to those skilled in the art. These alternatives are considered equivalents and are within the spirit and scope of the present invention.

That which is claimed is:

1. An improved method of purification of isophthalic acid comprising:
   (a) dissolving crude isophthalic acid in a feed solution comprising a polar solvent at a temperature of from about 100° C. to about 300° C.;
   (b) crystallizing the isophthalic acid by cooling the solution of step (a) to a temperature of from about 35° C. to about 120° C.;
   (c) separating the isophthalic acid crystals from the solution and drying the crystals; and
   (d) recycling about 20 percent to about 60 percent of the solution remaining after the separation of the isophthalic acid crystals back to the feed solution.

2. The method of claim 1 wherein the solution of step (d) which is recycled is about 25 percent.

3. The method of claim 1 wherein the temperature of step (a) is from about 200° C. to about 250° C.

4. The method of claim 1 wherein water is the polar solvent.

5. An improved method of purification of isophthalic acid comprising:
   (a) dissolving crude isophthalic acid in a feed solution comprising a polar solvent at a temperature of from about 100° C. to about 300° C.;
   (b) passing the hot feed solution containing isophthalic acid at a pressure sufficient to maintain the solution substantially in the liquid phase, through a particulate catalyst bed in the presence of hydrogen, the catalyst bed comprising at least one Group VIII noble metal-containing component selected from the group consisting of palladium-, platinum-, rhodium-, ruthenium-, osmium-, iridium-containing components and mixtures thereof supported on active carbon carrier particles;
   (c) cooling the solution to a temperature of from about 35° C. to about 120° C. to effect separation of the resulting purified isophthalic acid from the solution by crystallization;
   (d) recovering and drying the crystallized, purified isophthalic acid; and
   (e) recycling about 20 percent to about 60 percent of the solution remaining after the recovery of the isophthalic acid crystals back to the feed solution.

6. The method of claim 5 wherein the one or more of the Group VIII noble metal-containing components are supported on the same active carbon carrier particles and there is a substantially uniform distribution of one or more of the Group VIII noble metal-containing components throughout the catalyst bed.

7. The method of claim 5 wherein one of the Group VIII noble metal-containing components is supported on a first group of the active carbon carrier particles and a second Group VIII noble metal-containing component is supported on a second group of the active carbon carrier particles, and the aforesaid first group of particles is separate and distinct from the aforesaid second group of particles.

8. The method of claim 7 wherein the first group of particles comprises a rhodium-containing component and the second group of particles comprises a palladium-containing component.

9. The method of claim 7 wherein the first group of particles comprises a palladium-containing component and the second group of particles comprises a rhodium-containing component.

* * * * *

UNITED STATES PATENT OFFICE
CERTIFICATE OF CORRECTION

Patent No. 5,110,984          Dated May 5, 1992

Inventor(s) Rose M. Janulis

It is certified that error appears in the above-identified patent and that said Letters Patent is hereby corrected as shown below:

| Column | Line | |
|---|---|---|
| 1 | 4 | "WASTE-WATER TREATMENT A" should read --WASTE-WATER TREATMENT-- |
| 1 | 68 | "acid by pratical" should read --acid by practical-- |
| 4 | 31 | "the bromine ion releases" should read --the bromine ion released-- |
| 5 | 7 | "lower molecule weight" should read --lower molecular weight-- |
| 5 | 56 | "partial presure" should read --partial pressure-- |

Signed and Sealed this

Seventh Day of September, 1993

Attest:

BRUCE LEHMAN

Attesting Officer

Commissioner of Patents and Trademarks